US00RE47116E

(19) United States
(12) Reissued Patent
Aoki et al.

(10) Patent Number: US RE47,116 E
(45) Date of Reissued Patent: Nov. 6, 2018

(54) CONTROL APPARATUS FOR INTERNAL COMBUSTION ENGINE

(71) Applicant: TOYOTA JIDOSHA KABUSHIKI KAISHA, Toyota-shi, Aichi-ken (JP)

(72) Inventors: Keiichiro Aoki, Sunto-gun (JP); Hiroki Nishijima, Sunto-gun (JP)

(73) Assignee: TOYOTA JIDOSHA KABUSHIKI KAISHA, Toyota-shi, Aichi-ken (JP)

(21) Appl. No.: 15/365,299

(22) Filed: Nov. 30, 2016

Related U.S. Patent Documents

Reissue of:

(64) Patent No.: 8,943,809
Issued: Feb. 3, 2015
Appl. No.: 13/392,272
PCT Filed: Mar. 15, 2011
PCT No.: PCT/JP2011/056029
§ 371 (c)(1),
(2) Date: Feb. 24, 2012
PCT Pub. No.: WO2012/124054
PCT Pub. Date: Sep. 20, 2012

(51) Int. Cl.
*F01N 3/00* (2006.01)
*F02D 41/06* (2006.01)
(Continued)

(52) U.S. Cl.
CPC ..... *F02D 41/06* (2013.01); *F02D 41/1466* (2013.01); *F02D 41/1494* (2013.01);
(Continued)

(58) Field of Classification Search
CPC ..... F02D 41/1466; F02D 41/222; F02D 41/1494; F02D 41/06; F02D 41/22; F01N 2560/03; F01N 2560/05; G01N 15/06
(Continued)

(56) References Cited

U.S. PATENT DOCUMENTS

2009/0019918 A1 1/2009 Baars et al.
2009/0094963 A1 4/2009 Mizoguchi et al.
(Continued)

FOREIGN PATENT DOCUMENTS

DE 102 29 411 A1 1/2004
DE 102-29-441 A1 2/2004
(Continued)

OTHER PUBLICATIONS

International Search Report for PCT/JP2011/056029 dated Jun. 14, 2011.

*Primary Examiner* — William Doerrler
(74) *Attorney, Agent, or Firm* — Sughrue Mion, PLLC

(57) ABSTRACT

A control apparatus for an internal combustion engine detects an amount of particulate matter contained in an exhaust gas in an exhaust passage, according to an electrical property across electrodes of a particulate matter sensor disposed in the exhaust passage of the internal combustion engine. The term "electrical property" here refers to a property that changes with the amount of particulate matter deposited, for example, a current value of when a predetermined voltage is applied. After the internal combustion engine is started and detection of the amount of the particulate matter is completed, an element section of the particulate matter sensor is set to a predetermined temperature range. The particulate matter deposited on the element section is thereby burned and removed. The control apparatus maintains the element section in the predetermined
(Continued)

temperature range after burning and removing the particulate matter until the internal combustion engine stops.

10 Claims, 3 Drawing Sheets

(51) Int. Cl.
*F02D 41/14* (2006.01)
*G01N 15/06* (2006.01)
*F02D 41/22* (2006.01)

(52) U.S. Cl.
CPC ..... *G01N 15/0656* (2013.01); *F01N 2560/05* (2013.01); *F01N 2560/20* (2013.01); *F02D 41/222* (2013.01); *Y10S 55/10* (2013.01); *Y10S 55/34* (2013.01)

(58) Field of Classification Search
USPC ..... 60/295, 311; 95/8, 278; 96/417; 55/282.3, 523
See application file for complete search history.

(56) References Cited

U.S. PATENT DOCUMENTS

| | | | | |
|---|---|---|---|---|
| 2009/0126458 | A1* | 5/2009 | Fleischer et al. | 73/28.01 |
| 2011/0047985 | A1* | 3/2011 | Zawacki et al. | 60/286 |
| 2011/0314796 | A1* | 12/2011 | Nakamura | F01N 9/002 60/276 |

FOREIGN PATENT DOCUMENTS

| | | | |
|---|---|---|---|
| DE | 10 2007 014 761 | A1 | 10/2008 |
| DE | 10 2009 028 319 | A1 | 2/2011 |
| JP | 2007-304068 | A | 11/2007 |
| JP | 2008-190502 | A | 8/2008 |
| JP | 2008-547032 | A | 12/2008 |
| JP | 2010-151059 | A | 7/2010 |
| JP | 2010-275917 | A | 12/2010 |

* cited by examiner

CONTROL APPARATUS FOR INTERNAL COMBUSTION ENGINE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

[This application is a National Stage of International Application No. PCT/JP2011/056029 filed Mar. 15, 2011, the content of which is incorporated herein by reference in its entirety.] *This is a reissue application of U.S. Pat. No. 8,943,809, which was filed as U.S. patent application Ser. No. 13/392,272 on Feb. 24, 2012 and issued on Feb. 3, 2015, and which is a National Stage of Internal Application No. PCT/JP2011/056029 filed Mar. 15, 2011, the disclosure of which is incorporated herein by reference in its entirety.*

TECHNICAL FIELD

The present invention generally relates to control apparatuses for internal combustion engines. The present invention particularly relates to a control apparatus for an internal combustion engine including a particulate matter sensor, provided in an exhaust passage of the internal combustion engine, for detecting an amount of particulate matter in an exhaust gas.

BACKGROUND ART

Patent document 1, for example, discloses a sensor that detects an amount of particulate matter (hereinafter referred to also as "PM") contained in an exhaust gas of an internal combustion engine. The sensor disclosed in patent document 1 includes an insulating layer on which the PM is deposited and a pair of electrodes spaced apart from each other at the insulating layer. When the exhaust gas contacts with the sensor, PM in the exhaust gas is deposited between the electrodes. Conductivity across the electrodes varies in accordance with the amount of PM deposited, and resistance across the electrodes varies. Thus, the amount of PM deposited between the electrodes can be detected by detecting the resistance across electrodes of the sensor, and the amount of PM contained in the exhaust gas can be accordingly estimated to detect a fault in a PM trapping filter, etc.

If the amount of PM deposited between the electrodes exceeds a predetermined level in this sensor, a value of the resistance across the electrodes no longer changes. The sensor then cannot output a value corresponding to the amount of PM deposited. In such situation where a lot of PM deposit between the electrodes, in the technique disclosed in patent document 1, a PM reset that burns the deposited PM to remove them is performed by heating the sensor for a predetermined period of time with a heater embedded in the sensor.

PRIOR ART DOCUMENTS

Patent Document

Patent Document 1: JP-A-2008-190502

SUMMARY OF THE INVENTION

Problem to be Solved by the Invention

Upon the start of the internal combustion engine, condensate water stagnates in the exhaust passage. In such occasion, an element section of a PM sensor may get wet by the condensate water during the start-up of the internal combustion engine. If the element section is rapidly heated for PM reset while it is wet, cracking may occur at the element section of the PM sensor 8.

To prevent the cracking, during the start of the internal combustion engine, the PM sensor is typically heated and reactivated after confirming that the moisture in the exhaust passage is discharged and the exhaust passage is dry. However, this requires a considerable amount of time for completing the PM reset and switching to a PM amount detection mode after the start-up of the internal combustion engine. As a result, particularly after cold starting, if a short trip operation such that the system stops before the water temperature rises sufficiently is repeated, the PM sensor may not switch to the PM amount detection mode.

In order to establish the PM detection mode immediately after the start of the internal combustion engine, for example, the PM reset may be performed after stopping or before starting (preheat) the operation of the internal combustion engine. However, PM reset at such timing has a significant effect on battery load and it is also difficult to secure the time for PM reset.

An object of the present invention is to solve the foregoing problems and to provide a control apparatus for an internal combustion engine that is improved so that a PM amount can be measured at earlier timing in a start-up of the internal combustion engine.

Means for Solving the Problem

To achieve the foregoing object, a control apparatus for an internal combustion engine according to the present invention includes means for detecting an amount of particulate matter contained in an exhaust gas and means for burning to remove particulate matter deposited on an element section.

The means for detecting the amount of particulate matter detects an amount of particulate matter contained in an exhaust gas in an exhaust passage, according to an electrical property across electrodes of a particulate matter sensor disposed in the exhaust passage of the internal combustion engine. The term "electrical property" here refers to a property that changes with the amount of particulate matter deposited, for example, a current value of when a predetermined voltage is applied.

The means for burning and removing the particulate matter deposited on the element section burns and removes the particulate matter deposited on the element section by maintaining the element section of a particulate matter sensor in a predetermined temperature range after the internal combustion engine is started and detection of the particulate matter amount is completed. The term "predetermined temperature range" here refers to a temperature range in which the particulate matter deposited on the element section can be burned.

The control apparatus for an internal combustion engine according to the present invention further includes means for maintaining the element section in a predetermined temperature range after the particulate matter has been burned and removed until the internal combustion engine stops.

Preferably, the control apparatus for an internal combustion engine according to the present invention includes means for recording a parameter relating to a condition during the detection of the particulate matter amount. In this case, the control apparatus further includes means for determining, after the start of a current operation of the internal combustion engine, whether the detection of the particulate matter amount is completed in a preceding operation from the preceding start to the preceding stop of the internal combustion engine. The control apparatus in this case also includes means for reading, when the detection is determined to be uncompleted, the parameter recorded during the preceding operation. The means for detecting the particulate matter amount may be able to continue the detection of the particulate matter amount performed in the preceding operation according to the parameter after the start of the current operation of the internal combustion engine.

The control apparatus for an internal combustion engine according to the present invention may be such that, when the detection of the particulate matter amount performed in the preceding operation is to be continued as above and when a temperature in the exhaust passage is determined to be higher than a reference temperature after starting the current operation of the internal combustion engine, the means for detecting the particulate matter amount resumes the detection of the particulate matter amount performed in the preceding operation.

Effects of the Invention

In the present invention, the particulate matter is burned and removed after the detection of the particulate matter amount is completed. Thereafter, the temperature of the element section is maintained in a temperature range in which the particulate matter is burned until the internal combustion engine is stopped. This prevents the element section from being deposited with the particulate matter after completing the removal of the particulate matter. Since the element section is maintained in the temperature range until the preceding stop of the internal combustion engine, the detection of the particulate matter amount in the current start of the internal combustion engine can be started without the process for burning and removing the particulate matter of the sensor.

Even if the element section is wet due to the condensate water in the exhaust passage upon the start of the internal combustion engine, a temperature at which the particulate matter amount is detected is lower than a temperature at which the particulate matter is removed. Thus, element cracking is unlikely to occur. Detection of the particulate matter amount can therefore be immediately started without waiting for the condensate water to dry after the start of the internal combustion engine. This allows the particulate matter amount detection mode to be established at an early stage after the start of the internal combustion engine, so that an opportunity to detect the particulate matter amount can be secured even more reliably.

MODES FOR CARRYING OUT THE INVENTION

Figure 1:
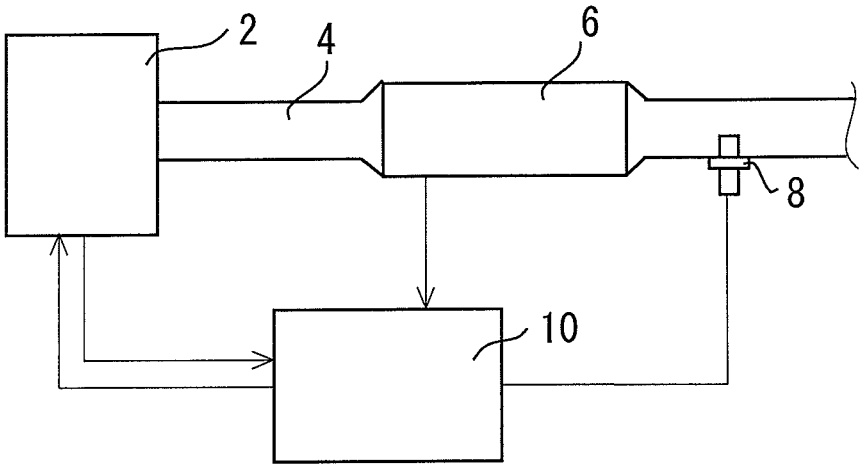
FIG. 1 is a schematic view showing general arrangements of a system according to the embodiment of the present invention.

An embodiment of the present invention will be described below with reference to the accompanying drawings. In each of the drawings, the same or corresponding parts are assigned the same reference numerals, and descriptions for those parts will be simplified or omitted.

Embodiment

[Arrangements of a System of the Embodiment]

FIG. 1 is a schematic view showing general arrangements of a system according to the embodiment of the present invention. In the system shown in FIG. 1, a DPF (diesel particulate filter) 6 is disposed in an exhaust passage 4 of an internal combustion engine 2. The DPF 6 traps particulate matter (PM) contained in an exhaust gas. A PM sensor 8 (particulate matter sensor) is disposed downstream of the DPF 6 of the exhaust passage 4. The PM sensor 8 detects an amount of PM contained in the exhaust gas that flows through the DPF 6.

The system includes a control apparatus 10. Various sensors, including the PM sensor 8, are connected to an input side of the control apparatus 10. Various actuators for the internal combustion engine 2 are connected to an output side of the control apparatus 10. The control apparatus 10 executes a predetermined program on the basis of input information sent from the various sensors and operates the various actuators to perform various controls related to the internal combustion engine 2.

Figure 2:
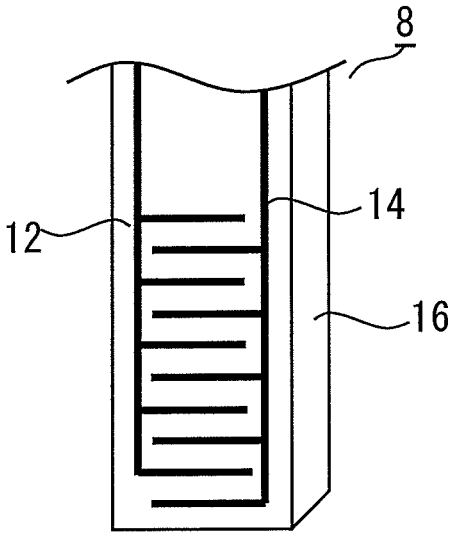
FIG. 2 is a schematic view showing an element section of the PM sensor according to the embodiment of the present invention.

FIG. 2 is an enlarged schematic view showing an element section of the PM sensor 8 according to the embodiment of the present invention. Referring to FIG. 2, the element section of the PM sensor 8 includes a pair of electrodes 12, 14 arranged on a surface thereof. The electrodes 12, 14 are disposed with a certain space between them so as not to contact with each other. In addition, each of the electrodes 12, 14 includes a comb-shaped portion and is disposed so that the comb shaped portions are interdigitated with each other. The electrodes 12, 14 are in contact with an insulating layer 16 formed directly therebeneath. The insulating layer 16 has a function of depositing the PM thereon. A heater not shown is embedded inside the insulating layer 16 in a layer below the electrodes 12, 14.

Each of the electrodes 12, 14 is connected to a power supply (not shown) via a power supply circuit, etc. Thus a predetermined voltage can be applied across the electrode 12 and the electrode 14. The heater is connected to the power supply (not shown) via the power supply circuit, etc. Thus a predetermined electric power is supplied to the heater and the element section can be heated. The power supply circuit, etc. are connected to and controlled by the control apparatus 10.

[Overview of Control According to the Embodiment]

Types of control performed by the control apparatus in this embodiment include detection of the PM amount contained in the exhaust gas, and a fault determination of the DPF 6 based on the PM amount. Specifically, the control apparatus 10 applies a predetermined voltage to detect the PM amount (hereinafter referred to as "trapping voltage")

across the electrodes 12, 14, and via a detector, detects a current value flowing through the PM sensor 8 as a sensor output.

When the trapping voltage is applied across the electrodes 12 and 14, the PM in the exhaust gas deposits between the electrodes 12, 14. As the amount of PM deposited between the electrodes 12, 14 increases, conducting portions between the electrodes 12, 14 increase, resulting in a smaller resistance across the electrodes 12, 14. In this embodiment, the sensor output from the PM sensor 8 is a value of a current flowing through the PM sensor 8, and the current value increases as the PM amount deposited between the electrodes 12, 14 increases. Accordingly, the PM amount contained in the exhaust gas can be detected by the PM sensor 8. A state in which the trapping voltage is applied and the current value is detected will hereunder also be referred to as "PM detecting mode". The element section is maintained at a temperature of 300° C. or less in the PM detecting mode.

In addition, the control apparatus 10 compares the detected sensor output with a criterion value to thereby determine whether there is a fault in the DPF 6. The criterion value is a value approximates to an upper limit value of the sensor output that corresponds to the amount of PM containable in the exhaust gas downstream of the DPF 6, when the DPF 6 is operating normally. The criterion value is found and set appropriately for each PM sensor 8 through experiments, etc. Therefore, if the sensor output is greater than the criterion value, it is determined that the PM amount discharged downstream of the DPF 6 is large and the DPF 6 is faulty.

Types of control performed by the control apparatus 10 further include a PM reset that removes the PM deposited on the element section of the PM sensor 8 by burning them. Specifically, in the above-mentioned fault determination of the DPF 6, the sensor output corresponding to the PM amount deposited on the element section for a predetermined period of time is compared with the criterion value. The PM deposited on the PM sensor 8 is therefore needed to be temporarily removed to start the fault determination of the DPF 6. The control apparatus 10 thus performs the PM reset such that removes the PM by burning them: that is, the control apparatus 10 energizes the heater, heats the element section of the PM sensor 8 to a temperature at which the PM is burned or higher, and maintains the temperature for a certain time. The temperature of the PM reset here is 500° C. or more.

[Characteristic Control of the Embodiment]

Upon the start of the internal combustion engine 2, condensate water may stagnate in the exhaust passage 4. If the PM sensor 8 is rapidly heated while it is wet due to the condensate water, the element section may crack. Therefore, the PM reset is typically performed after the internal combustion engine 2 has been started and the condensate water in the exhaust passage is gone. After the PM reset is completed, the PM sensor is switched to the PM detecting mode and the fault determination of the DPF is executed. In such cases, it is difficult to switch the PM sensor to the PM detecting mode at early timing after the start of the internal combustion engine.

If the PM is not deposited on the PM sensor 8 upon the start of the internal combustion engine 2, the PM detecting mode can be established immediately after the start without performing the PM reset. Further, the PM detecting mode is performed at a temperature of 300° C. or less, which is lower than the temperature in the PM reset. Cracking of the element section of the PM sensor 8 due to water soakage occurs when the element section is rapidly heated while it is wet. The cracking, however, is unlikely to occur at a temperature of about 300° C. in the PM detecting mode. Thus, if the PM is not deposited on the PM sensor 8 of the internal combustion engine 2, it is unnecessary to wait for the drainage and drying of the condensate water in the exhaust passage, and the PM detecting mode can be immediately established and the presence of a fault in the DPF 6 can be determined.

Accordingly in this embodiment, the following control is performed in order to establish the PM detecting mode immediately after the start of the internal combustion engine. The PM reset is performed when a fault determination of DPF 6 is completed after the start of the internal combustion engine. After completion of the PM reset, the element is maintained as is at the temperature of the PM reset (500° C. or more) until the internal combustion engine is stopped.

When the element is maintained at the temperature at the PM reset, the PM is burned, so the PM would not deposit on the element section. Therefore, a condition where the element section is free from the PM deposition can be maintained after the completion of the PM reset. If a preceding operation of the internal combustion engine is stopped in a state where the element section is kept free from the PM deposition as described above, in a current operation of the internal combustion engine 2, the fault determination for the DPF 6 can be immediately started in the start of the operation without performing the PM reset.

However, it is to be noted that, for example, the internal combustion engine 2 may be stopped during the execution of the fault determination for the DPF 6 in the preceding operation. In such cases where the internal combustion engine 2 is stopped during the execution of the fault determination of the DPF 6, the control apparatus 10 as well saves, in backup RAM, data such as a detection time in which the PM amount has been detected and operating condition parameters for correction of various outputs.

Then, after the internal combustion engine 2 is started for the current operation, information saved in the backup RAM is read and the detection of the PM amount succeeded from the preceding operation (the sequence to determine whether the DPF 6 is faulty) is continued without performing the PM reset. Since the temperature of the PM detecting mode is here maintained at 300° C. or less as well, the fault determination for the DPF 6 can be started immediately following the start of the internal combustion engine 2 without cracking the element.

Alternatively, for example, the internal combustion engine 2 in the preceding operation may be stopped in the middle of the PM reset after completing the fault determination for DPF 6. In this case, the PM reset needs to be performed to remove the PM from the element section after the internal combustion engine 2 is started for the current operation. The temperature during the PM reset needs to be increased to as high as 500° C. or more. Following the start of the internal combustion engine 2, the PM reset is performed after conditions required for starting the reset, such as a condition required for avoiding water soakage of the PM sensor 8, are satisfied. The fault determination for the DPF 6 is then performed while the PM is free from the element section. After the fault determination for the DPF 6 is completed, the PM reset is performed again as described above. Following the completion of the PM reset, the element section is maintained at the temperature of the PM reset until the internal combustion engine 2 is stopped in the current operation.

[Specific Control Routine of the Embodiment]

Figure 3:
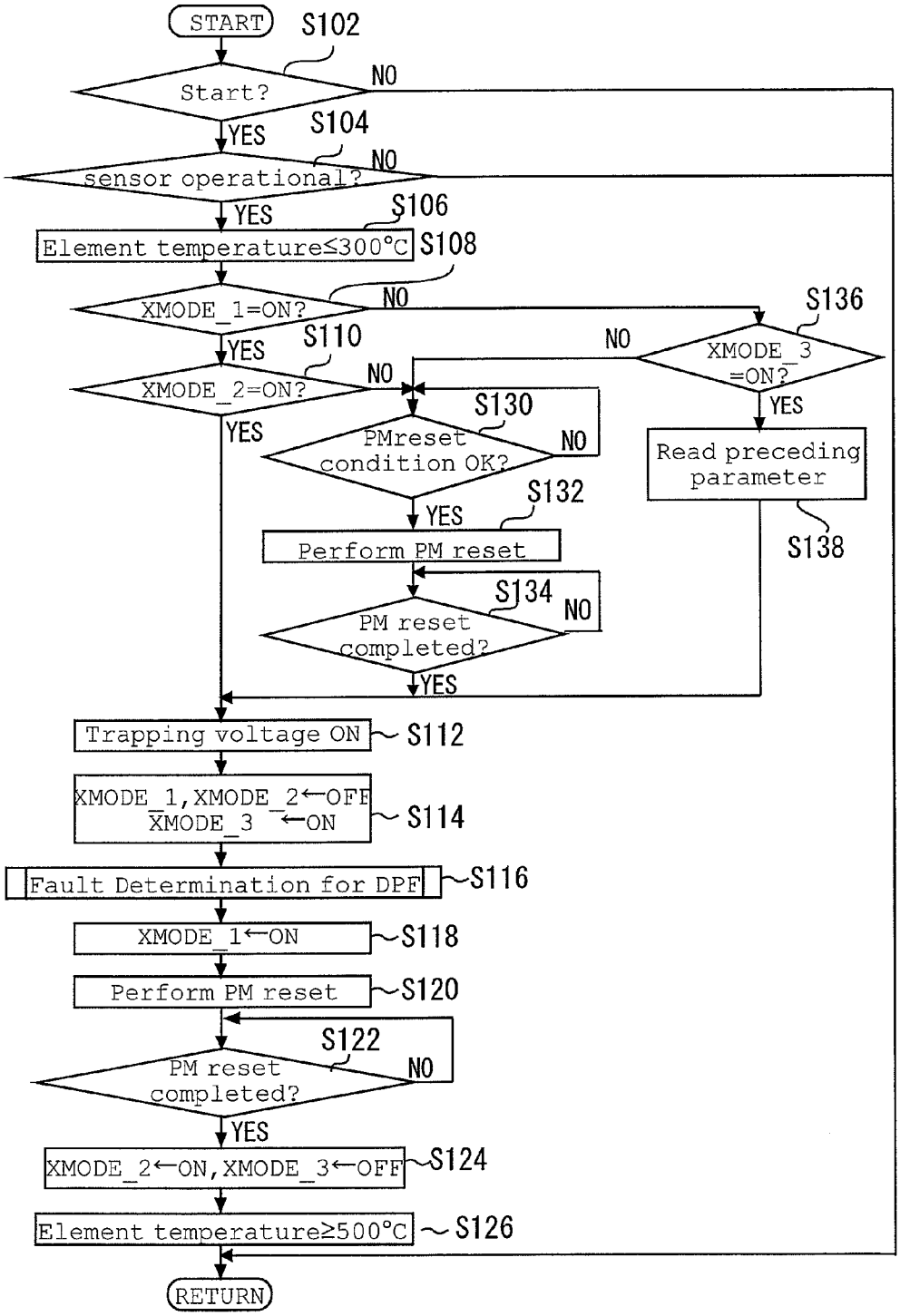
FIG. 3 is a flow chart illustrating a control routine performed by the control apparatus in the embodiment of the present invention.

FIG. 3 is a flow chart illustrating a control routine performed by the control apparatus in the embodiment of the present invention. The routine shown in FIG. 3 is repeatedly performed at predetermined intervals. In the routine of FIG. 3, first, whether the internal combustion engine 2 has been started is determined (S102). If it is determined that the internal combustion engine 2 has not started, the control is directly terminated.

If it is determined that the internal combustion engine 2 has been started in step S102, whether the sensor is operational is next determined (S104). If it is determined that the PM sensor 8 is not operational, the control is directly terminated.

If it is determined that the PM sensor 8 is operational in step S104, the sensor temperature is next maintained at 300° C. or less (S106). This temperature is equivalent to that of the operational environment in which the PM sensor 8 usually operates to detect the PM and basically no heat is applied by the heater, etc.

Next, whether a flag XMODE_1 is ON is determined (S108). By default, the flag XMODE_1 is OFF and, remains OFF from the start of the fault determination for the DPF 6 till its completion. If it is determined that XMODE_1=ON holds, the fault determination is confirmed to be completed before the internal combustion engine is stopped in the preceding operation.

If it is determined in step S108 that XMODE_1=ON holds, whether a flag XMODE_2 is ON is determined (S110). By default, the flag XMODE_2 is OFF and, according to the process described in detail later, remains OFF from the start of the fault determination for the DPF 6 till the completion of the PM reset. If it is determined that XMODE_2=ON holds, both the fault determination and the PM reset is confirmed to be completed before the internal combustion engine 2 is stopped in the preceding operation.

If it is determined in step S110 that XMODE_2=ON holds, the trapping voltage is applied and trapping of PM is started (S112). The application of a predetermined trapping voltage across the electrodes 12, 14 is here started according to a predetermined control signal from the control apparatus 10, and the output from the PM sensor 8 is detected.

Next, XMODE_1 and XMODE_2 are turned OFF and XMODE_3 is turned ON (S114). XMODE_3 is a flag that is OFF by default and is turned ON from the start of the fault determination till the completion of the PM reset described later.

The fault determination for the DPF 6 is next performed (S116). In the fault determination for the DPF 6, the output from the PM sensor 8 is detected after a predetermined time has passed from the start of the application of the trapping voltage, and the output is compared with the reference value. The DPF 6 is determined to be faulty if the sensor output is greater than the reference value. The fault determination for the DPF 6 is controlled according to a fault determination performance routine. During the performance of the fault determination, data such as an elapsed time in the PM detection and operating condition parameters for correction of various outputs are saved in the backup RAM.

When the fault determination in step S116 is completed, the flag XMODE_1 is turned ON (S118). This indicates that the fault determination is completed during the current operation of the internal combustion engine 2.

Next, the PM reset is performed (S120). Specifically, the heater is energized according to a control signal from the control apparatus 10 to thereby heat the element section to a predetermined temperature or more. The PM deposited on the element section of the PM sensor 8 is burned and removed.

Then, whether the PM reset is completed is determined (S122). If it is determined that the PM reset is not yet completed, the determination for the PM reset completion in step S122 is repeated at predetermined intervals with the PM reset being performed.

If it is determined in step S122 that the PM reset is completed, the flag XMODE_2 is turned ON and the flag XMODE_3 is turned OFF (S124). This indicates that the sequence is completed up to the PM reset during the current operation of the internal combustion engine 2.

Next, the sensor temperature is maintained at 500° C. or more (S126). Since the temperature at the PM reset is here 500° C. or more, the temperature of the element section is maintained as is at 500° C. or more after the PM reset. The PM does not deposit on the element section in this temperature range. That is to say, the condition in step S124 where the PM on the PM sensor 8 has been burned is maintained.

The current routine is then terminated. If the internal combustion engine 2 is stopped after the end of step S126 as above, the PM detection (fault determination) in the subsequent operation can be performed immediately after the start of the internal combustion engine 2.

Meanwhile, if the routine in the preceding operation of the internal combustion engine 2 is terminated after execution of the PM reset in step S120 and before completing the PM reset in step S122 with the stop of the internal combustion engine, the flag XMODE_1 is ON and the flag XMODE_2 is OFF. In this case, when the internal combustion engine 2 for the current operation is started and the routine is executed, XMODE_2=ON does not hold in step S110.

The element section of the PM sensor 8 is considered to be deposited with the PM, and the PM reset needs to be performed before starting the fault determination. Therefore, when XMODE_2=ON does not hold in step S110, it is then determined in step S130 whether the condition for the PM reset is satisfied. Specifically, the condition for the PM reset includes those for avoiding water soakage by the condensate water. For example, whether the temperature of the wall or a portion at which the condensate water stagnates in the exhaust passage 4 is at dew point or 100° C. or more. Such a condition is preset and stored in the control apparatus 10 in advance.

If the condition for the PM reset is determined to be unsatisfied, the process in step S130 for determining whether the condition is satisfied is repeated at predetermined intervals until the condition is satisfied. On the other hand, if the condition for the PM reset is determined to be satisfied in step S130, the PM reset is performed (S132). Specifically, the heater is energized by a control signal from the control apparatus 10 to thereby heat the element section to a predetermined temperature.

The completion of the PM reset is next determined (S134). If the PM reset is determined uncompleted, the process in step S134 for determining the completion of the PM reset is repeated.

On the other hand, if the PM reset is determined to be completed in step S134, it is determined that the PM deposit on the element section is removed and the fault determination can be performed. The process then moves to step S112 and control according to the processes of steps S112 to S126 is executed.

In another case, the routine may be terminated during the fault determination of step S116 with the stop of the internal combustion engine 2. The flag XMODE_1 then remains OFF as it has been turned OFF in step S114. Then, XMODE_1=ON does not hold in step S108 in the routine of the current operation after starting the internal combustion engine 2.

In this case, whether the flag XMODE_3 is ON is next determined (S136). In step S114, the flags XMODE_1 and XMODE_2 are turned OFF and at the same time XMODE_3 is turned ON. XMODE_1 is reversed in step S118 in prior to XMODE_2 and XMODE_3 and is turned ON. Accordingly, when XMODE_1 is OFF and XMODE_3 is OFF, it indicates that the PM reset has never been completed before.

Therefore, when XMODE_3=ON does not hold in step S136, the first PM reset for the PM sensor 8 is performed according to processes of steps from S130 to S134. Control according to processes of steps from S112 to S126 is performed after that.

On the other hand, when XMODE_3=ON holds in step S136, the preceding operation of the internal combustion engine 2 is considered to be stopped during the process of the fault determination for the DPF 6. In this case, a parameter, etc. recorded in the preceding fault determination is read (S138). The information is added and the control is passed onto step S112. The fault determination interrupted in the preceding operation is resumed and processes of steps from S112 to S126 are performed in sequence.

As described heretofore, in this embodiment, the fault determination and the PM reset are performed once in one trip from the start to the stop of the internal combustion engine 2. The PM sensor 8 is maintained at 500° C. or more after the PM reset so that the PM does not deposit on the element section. The fault determination can be thus performed immediately after the start of the internal combustion engine 2 in the next operation, without waiting for the drainage of the condensate water. The period of time from the start of the internal combustion engine 2 to the completion of the fault determination can be shortened, and the fault determination can be therefore performed even if one trip is relatively short, achieving more opportunities to perform the fault determination.

[Another Control Example of this Embodiment]

Figure 4:
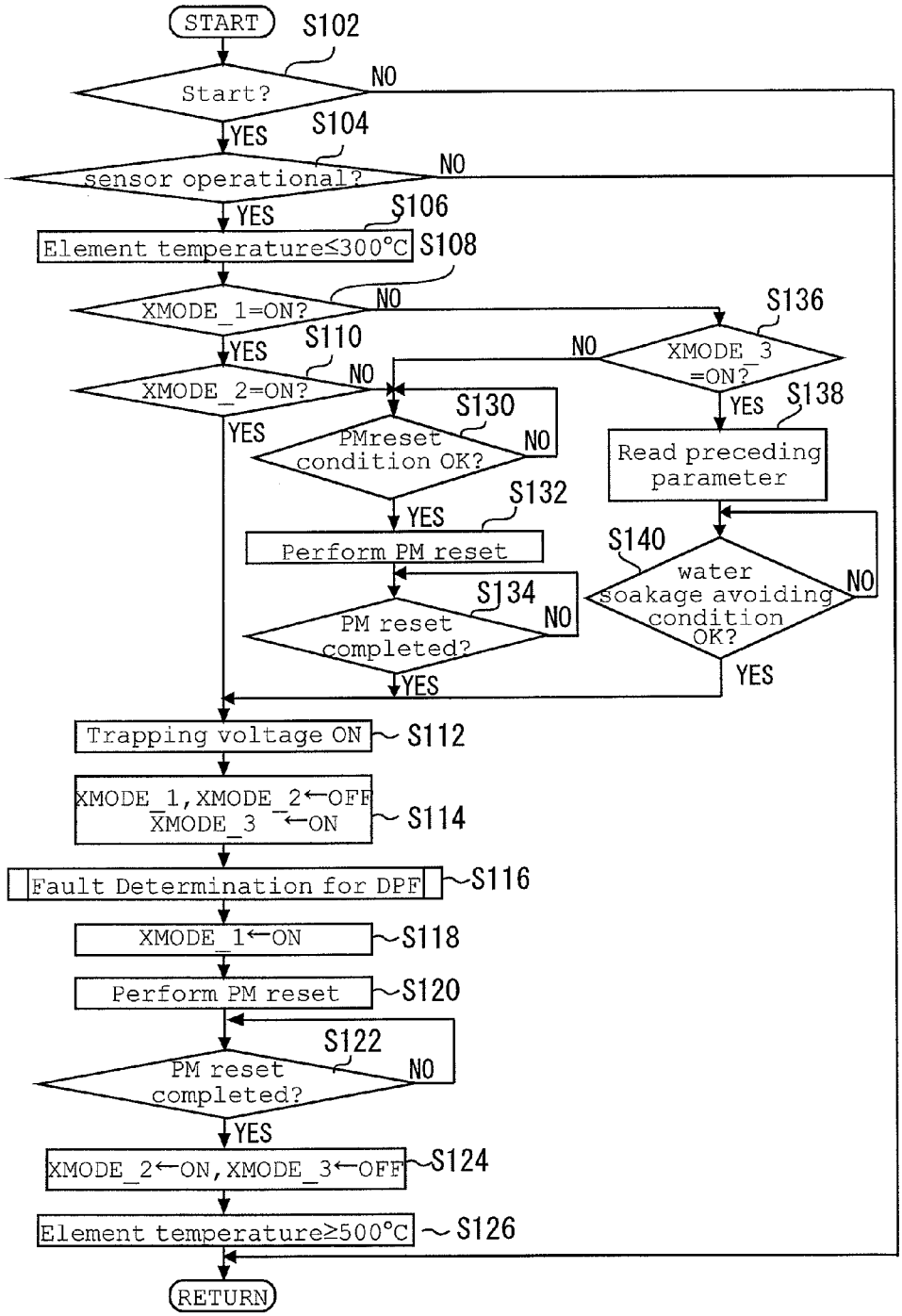
FIG. 4 is a flow chart for illustrating another control routine performed by the control apparatus in the embodiment of the present invention.

The embodiment has been described for the case in which the trapping voltage is applied in step S112 immediately after the parameter is read in step S138. The present invention is however not limited to this. FIG. 4 is a flow chart for illustrating another control routine performed by the control apparatus in the embodiment of the present invention.

The routine shown in FIG. 4 is the same as the routine shown in FIG. 3, except that the routine of FIG. 4 includes a process of step S140 after the process of step S138 before the process of step S112. In the routine shown in FIG. 4, after the parameter in the preceding operation is read in step S138, whether the condition for avoiding water soakage in the PM detecting mode is satisfied is determined in step S140. The condition for avoiding the water soakage includes, for example, whether the temperature of the wall or a portion at which the condensate water stagnates is at the dew point or 100° C. or more. Such a condition is preset and stored in the control apparatus 10 in advance.

If the condition is determined to be unsatisfied in step S140, the process in step S140 for determining whether the condition is satisfied is repeated. If on the other hand the condition is determined to be satisfied in step S140, the control is passed onto step S112 and the fault determination succeeded from the preceding operation is continued.

In addition, the fault determination for the DPF 6 is performed as the PM detecting mode after the start of the engine in the embodiment. The present invention is however not limited to the case of performing the fault determination for the DPF 6. The present invention is also effective in detecting the PM amount contained in the exhaust gas as the PM detecting mode at an early stage after the start of the engine.

Additionally, the embodiment has been described for the case in which the temperature during the PM reset and after completing the reset are both set to 500° C. or more. This is the temperature effective for burning the PM deposited on the element section. However, the temperature range for burning the particulate matter in the present invention is not limited to 500° C. or more, and may be appropriately set according to the amount of particulate matter deposition or components of the particulate matter or other factors.

Further, the temperature during the PM detecting mode is described as 300° C. or less in the embodiment. The temperature during detection of the PM in the present invention is not limited to this. However, the temperature during the PM detection is to be lower than the temperature during the PM reset and in a range the element section is unlikely to crack even if the element section is wet.

The numerals of the number of the elements, quantity, volume, ranges, etc. referred in the foregoing embodiment are not limited to them in the present invention unless expressly described or a numeral is apparently a certain number in principle. Further, the structures and steps of the embodiment illustrated are not always essential to the present invention except for those expressly described or a structure or a step that is limited to a certain one in principle.

Description of Notations

2 internal combustion engine
4 exhaust passage
6 DPF (diesel particulate filter)
8 PM sensor
10 control apparatus

The invention claimed is:

1. A control apparatus for an internal combustion engine, comprising:

means for detecting an amount of particulate matter contained in an exhaust gas in an exhaust passage of the internal combustion engine according to an electrical property across electrodes of a particulate matter sensor disposed in the exhaust passage of the internal combustion engine;

means for burning and removing the particulate matter deposited on an element section of the particulate matter sensor by setting the element section in a predetermined temperature range for burning and removing the particulate matter deposited on the element section so as to maintain the element section in a condition in which particulate matter does not deposit on the element section, after the internal combustion engine is started and detection of the particulate matter amount is completed; and

[means for maintaining] *wherein the means for burning and removing the particulate matter maintains* the element section at the predetermined temperature range continuously after the particulate matter has been removed by burning until the internal combustion engine stops.

2. The control apparatus for an internal combustion engine according to claim 1, further comprising:

means for recording [a parameter] *parameters* relating to a condition for the detection of the particulate matter amount;

means for determining, after a start of a current operation of the internal combustion engine, whether the detection of the particulate matter amount [is] *was* completed in a preceding operation [from the start to the stop] of the internal combustion engine; and means for reading a parameter recorded during the preceding operation among the parameters recorded by the means for recording when the detection of the particulate matter amount is determined to be uncompleted in the preceding operation, wherein:

the means for detecting the particulate matter amount continues the detection of the particulate matter amount performed in the preceding operation according to the parameter recorded during the preceding operation, after the start of the current operation of the internal combustion engine.

3. The control apparatus for an internal combustion engine according to claim 2, wherein:

the means for detecting the particulate matter amount resumes the detection of the particulate matter amount preformed in the preceding operation, when a temperature in the exhaust passage is determined to be higher than a reference temperature after the start of the current operation of the internal combustion engine.

4. A control apparatus for an internal combustion engine, comprising:

a detection device that detects an amount of particulate matter contained in an exhaust gas in an exhaust passage of the internal combustion engine according to an electrical property across electrodes of a particulate matter sensor disposed in the exhaust passage of the internal combustion engine;

a device that burns and removes the particulate matter deposited on an element section of the particulate matter sensor by setting the element section in a predetermined temperature range for burning and removing the particulate matter deposited on the element section so as to maintain the element section in a condition in which particulate matter does not deposit on the element section, after the internal combustion engine is started and detection of the particulate matter amount is completed; and

[a] *wherein the* device that *burns and removes the particulate matter* maintains the element section at the predetermined temperature range continuously after the particulate matter has been removed by burning until the internal combustion engine stops.

5. The control apparatus for an internal combustion engine according to claim 4, further comprising:

a record device that records [a parameter] *parameters* relating to a condition for the detection of the particulate matter amount;

a device that determines, after a start of a current operation of the internal combustion engine, whether the detection of the particulate matter amount [is] *was* completed in a preceding operation [from the start to the stop] of the internal combustion engine; and a device that reads a parameter recorded during the preceding operation among the parameters recorded by the record device when the detection of the particulate matter amount is determined to be uncompleted in the preceding operation, wherein:

the detection device continues the detection of the particulate matter amount performed in the preceding operation according to the parameter recorded during the preceding operation, after the start of the current operation of the internal combustion engine.

6. The control apparatus for an internal combustion engine according to claim 5 wherein:

the detection device resumes the detection of the particulate matter amount preformed in the preceding operation, when a temperature in the exhaust passage is determined to be higher than a reference temperature after the start of the current operation of the internal combustion engine.

*7. A control apparatus for an internal combustion engine, comprising:*

*means for detecting an amount of particulate matter contained in an exhaust gas in an exhaust passage of the internal combustion engine according to an electrical property across electrodes of a particulate matter sensor disposed in the exhaust passage of the internal combustion engine;*

*means for burning and removing the particulate matter deposited on an element section of the particulate matter sensor by setting the element section in a predetermined temperature range for burning and removing the particulate matter deposited on the element section so as to maintain the element section in a condition in which particulate matter does not deposit on the element section, after the internal combustion engine is started and detection of the particulate matter amount is completed;*

*wherein the means for burning and removing the particulate matter maintains the element section in a second temperature range lower than the predetermined temperature range after the particulate matter has been removed, the second temperature range being a range in which the particulate matter sensor is able to detect the amount of particulate matter;*

*means for recording parameters relating to a condition for the detection of the particulate matter amount;*

*means for determining, after a start of a current operation of the internal combustion engine, whether the detection of the particulate matter amount was completed in a preceding operation of the internal combustion engine; and*

*means for reading a parameter recorded during the preceding operation among the parameters recorded by the means for recording when the detection of the particulate matter amount is determined to be uncompleted in the preceding operation, wherein:*

*the means for detecting the particulate matter amount continues the detection of the particulate matter amount performed in the preceding operation according to the parameter recorded during the preceding operation, after the start of the current operation of the internal combustion engine.*

*8. The control apparatus for an internal combustion engine according to claim 7, wherein:*

*the means for detecting the particulate matter amount resumes the detection of the particulate matter amount preformed in the preceding operation, when a temperature in the exhaust passage is determined to be higher than a reference temperature after the start of the current operation of the internal combustion engine.*

*9. A control apparatus for an internal combustion engine, comprising:*

*a detection device that detects an amount of particulate matter contained in an exhaust gas in an exhaust passage of the internal combustion engine according to an electrical property across electrodes of a particulate matter sensor disposed in the exhaust passage of the internal combustion engine;*

*a device that burns and removes the particulate matter deposited on an element section of the particulate*

*matter sensor by setting the element section in a predetermined temperature range for burning and removing the particulate matter deposited on the element section so as to maintain the element section in a condition in which particulate matter does not deposit on the element section, after the internal combustion engine is started and detection of the particulate matter amount is completed;*

*wherein the device that burns and removes the particulate matter maintains the element section in a second predetermined temperature range lower than the predetermined temperature range after the particulate matter has been removed, the second predetermined temperature range being a range in which the particulate matter sensor is able to detect the amount of particulate matter;*

*a record device that records parameters relating to a condition for the detection of the particulate matter amount;*

*a device that determines, after a start of a current operation of the internal combustion engine, whether the detection of the particulate matter amount was completed in a preceding operation of the internal combustion engine; and*

*a device that reads a parameter recorded during the preceding operation among the parameters recorded by the record device when the detection of the particulate matter amount is determined to be uncompleted in the preceding operation, wherein:*

*the detection device continues the detection of the particulate matter amount performed in the preceding operation according to the parameter recorded during the preceding operation, after the start of the current operation of the internal combustion engine.*

*10. The control apparatus for an internal combustion engine according to claim 9, wherein:*

*the detection device resumes the detection of the particulate matter amount preformed in the preceding operation, when a temperature in the exhaust passage is determined to be higher than a reference temperature after the start of the current operation of the internal combustion engine.*

* * * * *